Figure 1:
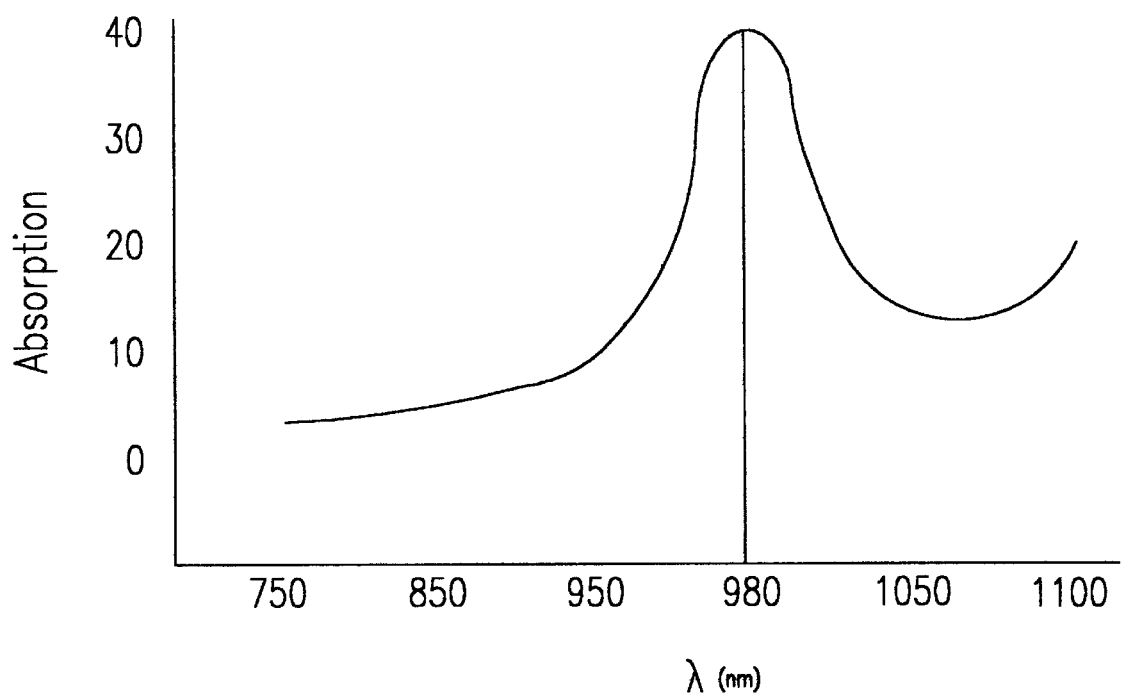

United States Patent [19]
Moran et al.

[11] Patent Number: 5,941,701
[45] Date of Patent: Aug. 24, 1999

[54] DEVICE AND METHOD TO TREAT ORAL DISEASE IN FELINES

[76] Inventors: Kelly Moran, 495 Main St.; Jane Morello, 89 Springfield St., both of Wilbraham, Mass. 01095; Bill Siminovsky, 1301 Trumansburg Rd., Ithaca, N.Y. 14850; Carol Morello, 495 Main St., Wilbraham, Mass. 10195; Kimberly A. Muller, 16 Puritan Valley, Brookfield, Conn. 06804

[21] Appl. No.: 09/114,990

[22] Filed: Jul. 14, 1998

[51] Int. Cl.$^6$ ................................................. A61D 5/00
[52] U.S. Cl. ...................... 433/1; 433/215; 433/141; 433/29; 606/2; 606/15
[58] Field of Search ................. 433/1, 215, 29, 433/216, 229, 226, 141; 606/2, 3, 10, 15, 16, 14, 13; 128/898

[56] References Cited

U.S. PATENT DOCUMENTS

| | | | |
|---|---|---|---|
| 4,940,411 | 7/1990 | Vassiliadis et al. | 433/215 |
| 5,382,163 | 1/1995 | Putnam | 433/215 |
| 5,388,987 | 2/1995 | Badoz et al. | 433/29 |
| 5,409,376 | 4/1995 | Murphy | 433/29 |
| 5,474,449 | 12/1995 | Loge et al. | 433/29 |
| 5,611,793 | 3/1997 | Wilson et al. | 606/2 |
| 5,616,141 | 4/1997 | Cipolla | 606/15 |
| 5,636,983 | 6/1997 | Shoji et al. | 433/29 |
| 5,658,148 | 8/1997 | Neuberger et al. | 433/215 |
| 5,758,678 | 4/1998 | Patel | 606/10 |

*Primary Examiner*—Gene Mancene
*Assistant Examiner*—Pedro Philogene
*Attorney, Agent, or Firm*—Bolesh J. Skutnik; BJ Associates

[57] ABSTRACT

A laser system and method are described that will effectively interrupt the progression of periodontal disease in felines, particularly in situations where the disease has progressed to advanced stages of periodontitis and feline lymphocytic-plasmacytic gingivitis stomatitis. A laser system is employed to achieve precision in surgical procedures where the working field is limited due to the anatomical structure of a feline's mouth. The laser system is also capable of effectively sealing tubules and of eradicating bacteria in the periodontium to significantly reduce the risk of infection. Additionally, the laser therapy can be preceded by pretreatment methods to effectively interrupt the progression of periodontal diseases.

20 Claims, 3 Drawing Sheets

DEVICE AND METHOD TO TREAT ORAL DISEASE IN FELINES

BACKGROUND OF THE INVENTION

1. Field of the Invention

The present invention relates to a device and method to treat periodontal disease in felines, particularly in situations where the disease has progressed to advanced stages of periodontitis and feline lymphocytic-plasmacytic gingivitis (commonly referred to as feline lymphocytic-plasmacytic stomatitis).

2. Information Disclosure Statement

Oral diseases are especially prevalent in cats. Periodontal disease can range from a localized inflammation of the gingiva (gingivitis) to inflamation and destruction of the gingiva, alveolar bone, the periodontal ligament, and tooth structure (periodontitis). Etiology of the disease can involve plaque, calculus, and systemic inflammatory response.

Generally, the protocol for treating periodontal disease focuses on cleaning the oral cavity, repairing the tissue, and stopping the progression of the disease. However, the available treatment methods, which include scalping, polishing, curettage, dental extractions, root planing, gingivectomies and in extreme cases, gingival flaps or grafts, are inadequate when treating advanced periodontitis and feline lymphocytic-plasmacytic gingivitis/stomatitis.

Root planing is often necessary to remove necrotic tissue from the roots of periodontally involved teeth. A curette or Orban file is applied to the root surface and withdrawn in overlapping strokes using sufficient pressure to scrape necrotic cementum and debris from the root and smooth its surface. However, due to the anatomical structure of a cat's mouth, it is very difficult to remove the necrotic debris without affecting the surrounding soft tissue.

A gingivectomy is often performed to eliminate gingival sulcus, in an effort to facilitate plaque control and oral hygiene. A gingivectomy is required where pocket depths exceed 4 mm, the epithelial attachment is still above bone level, and resection can be contained within the attached gingiva. The level of epithelial attachment is determined using a periodontal probe and is marked on the buccal surface of the gingiva. The gingival tissue is then excised using a periodontal knife. Digital pressure is usually sufficient to effect hemostasis. However, the gingiva is especially narrow in cats therefore, it is very difficult to limit resection to the attached gingiva. Additionally, the anatomical structure of a feline's mouth limits the available working area and restricts maneuverability of instruments within the mouth thereby reducing the precision by which the procedure can be performed.

Cats exhibit particular manifestations of periodontal disease that are unique to the feline species. For example, a chronic problem in cats that is commonly associated with both chronic gingivitis/periodontitis and feline lymphocytic-plasmacytic stomatitis is external root resorption. Inflammatory resorption occurs at the cementoenamel junction. The presence of exuberant gingival tissue often conceals extensive cavitations in the tooth that undermine the crown eventually causing it to fracture and crumble thereby exposing the dentin. Exposed dentin is sensitive and extremely painful.

Typically, a fluoride gel is administered to treat this condition to desensitize the dentin. However, restoration has not been very successful and in many circumstances all of the teeth must be extracted. Extraction of involved teeth is often difficult because the crowns are weakened and therefore tend to fracture easily. Additionally, the roots are usually ankylosed and hard to separate from the surrounding bone. The long-term therapeutic response for treating external root resorption has typically been poor.

The cats are also placed on systemic antibiotics and long-term corticosteroids to reduce the risk of infection and to reduce inflammation. However, antibiotic treatments are usually not effective in treating feline lymphocytic-plasmacytic gingivitis/stomatitis because a primary bacterial causative agent has not yet been identified and long-term corticosteroid use can lead to serious secondary systemic side effects such as kidney failure.

Thus there is a need for a device and method that will improve treatment for cats with periodontal disease, particularly in the advanced stages of periodontitis and feline lymphocytic-plasmacytic stomatitis without the complications associated with the prior art.

OBJECTS AND SUMMARY OF THE INVENTION

It is an object of the present invention to provide a laser system and treatment method that will eliminate the complications associated with the prior art.

It is another aim of the present invention to eliminate the chronic symptoms associated with periodontal disease in cats.

It is another aim of the present invention to employ a laser system to achieve enhanced precision in surgical procedures.

It is a further aim of the present invention to seal the tubules in surrounding tissue and eradicate bacteria to significantly reduce the risk of infection.

Briefly stated, the present invention describes a laser system and method that will effectively interrupt the progression of periodontal disease in cats, particularly in situations where the disease has progressed to advanced stages of periodontitis and feline lymphocytic-plasmacytic stomatitis. A laser system is employed to achieve precision in surgical procedures where the working field is limited due to the anatomical structure of a cat's mouth. The laser system is also capable of effectively sealing tubules and of eradicating bacteria in the periodontium to significantly reduce the risk of infection. Additionally, the laser therapy can be preceded by pre-treatment methods to effectively interrupt the progression of periodontal diseases.

The above, and other objects, features, and advantages of the present invention will become apparent from the following detailed description read in conjunction with the accompanying drawings.

BRIEF DESCRIPTION OF THE EMBODIMENTS

FIG. 1 Graph depicting $H_2O$ absorption spectra in wavelength of interest

Figure 2:
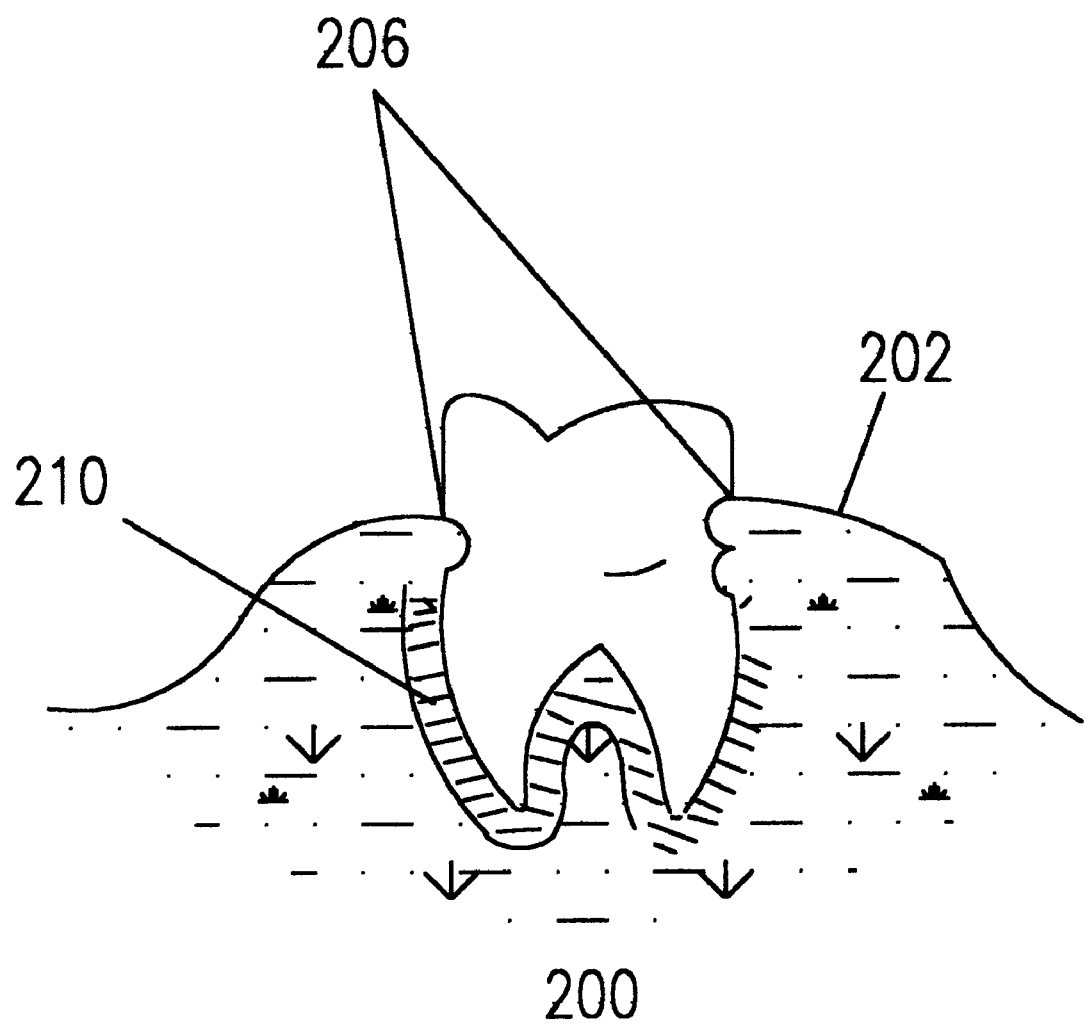

FIG. 2 Cross-section of mandibular molar afflicted with external root resorption.

Figure 3:
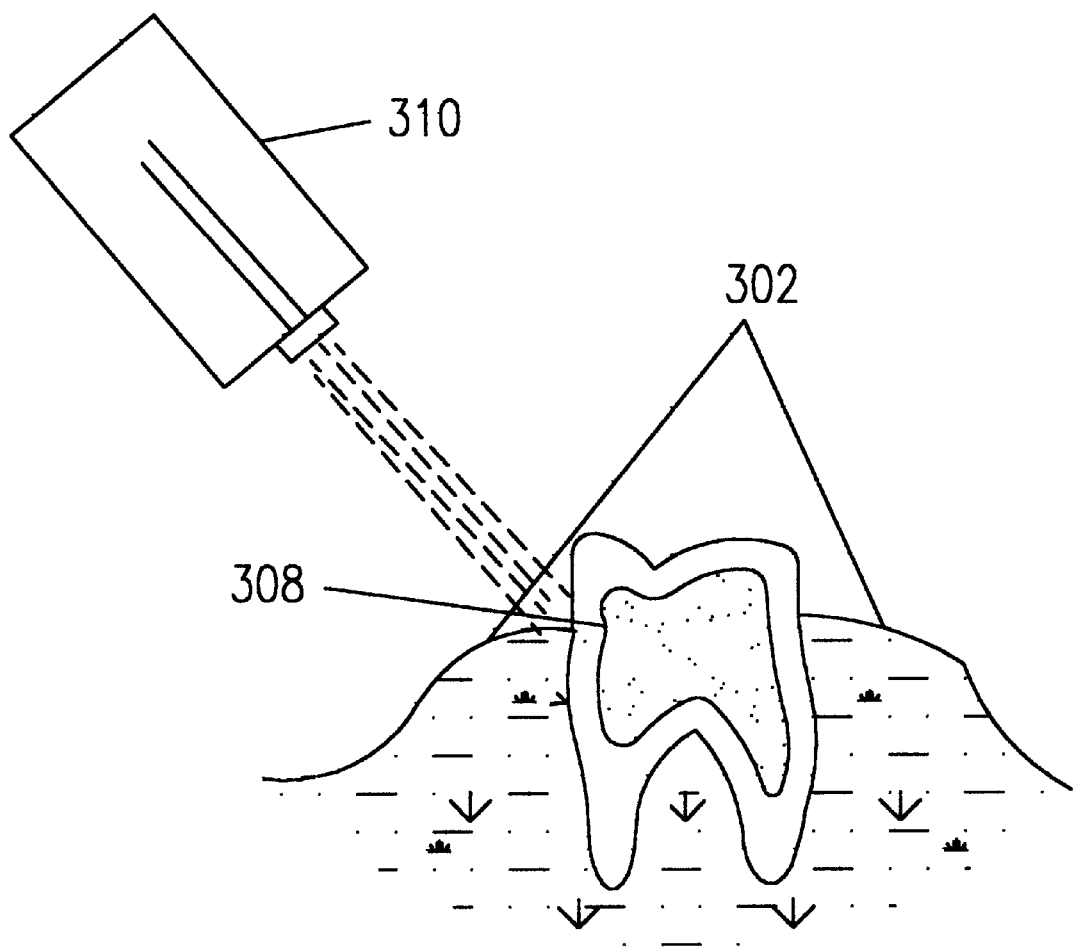

FIG. 3 Schematic view of laser system used to treat feline lymphocytic-plasmacytic gingivitis/stomatitis.

DISCLOSURE OF PREFERRED EMBODIMENTS

The present invention describes a new device and method to treat periodontal disease, particularly in situations where the disease has progressed to periodontitis and feline lymphocytic-plasmacytic stomatitis.

A preferred embodiment of the present invention employs a 980 nm diode laser to achieve high precision, low penetration cutting. The graph in FIG. 1 illustrates a peak in the absorption of light in water in the vicinity of 980 nm. As a result, 980 nm radiation is preferred over 1064 nm radiation for medical procedures involving soft tissue because greater absorption is achieved when 980 nm light is employed on the tissue.

FIGS. 2 and 3 illustrate an example and preferred embodiment in which the present invention was used to treat feline lymphocytic-plasmacytic gingivitis/stomatitis. Feline lymphocytic-plasmacytic gingivitis (also known as feline plasma cell gingivitis-pharyngitis and chronic feline gingivitis-stomatitis) is an oral disease of unknown etiology that is frequently encountered in cats. Cats with feline lymphocytic-plasmacytic gingivitis stomatitis have proliferative and ulcerated gingiva that extends into the soft palate and oropharynx. The gingiva may recede, there may be bone loss, the roots may become exposed, and abscesses may form. Cats with feline lymphocytic-plasmacytic gingivitis/stomatitis suffer from intense oral pain that is typically attributable to external root resorption.

FIG. 2 is a cross-sectional view of a mandibular molar that is afflicted with external root resorption. The presence of exuberant gingival tissue 202 conceals extensive cavitations 206 in tooth 200 that undermines crown 210 eventually causing it to fracture and crumble. In typical current treatments, tooth 200 would be extracted. Generally, the response to extractions is favorable. However, extractions are not always successful for treating external root resorption when the cat has feline lymphocytic-plasmacytic stomatitis. Approximately 20% of the cats with feline lymphocytic-plasmacytic stomatitis experience a relapse following the extraction and the long-term response is typically poor.

FIG. 3 shows a preferred embodiment of the present invention in which a 980 nm diode laser 310 was used to treat a cat with feline lymphocytic-plasmacytic gingivitis stomatitis who had relapsed following extraction. Laser 310 was set to deliver an optical power of 2 W to resect gingiva 302 to the cementoenamel junction 308 and effectively eliminate the affected tissue. A 600 µm flat tip optical fiber 302 delivered radiation to the affected tissue in a continuous mode. A small spot size was used to concentrate high amounts of energy into the tissue to achieve rapid vaporization.

After the resection, the laser was then set to 1 W (pulsed 1 sec on/1 sec off) to seal the tubules thereby preventing the osmotic action of the tubules from replanting bacteria, present at the time of the procedure, into the newly grown tissue.

In another example and preferred embodiment of the present invention, a diode laser system with multi-wavelength sources may be employed in conjunction with a photosensitizer to stop the progression of periodontitis. Generally, 980 nm light may be employed to resect the affected tissue and a wavelength that is suitable to activate the photosensitizer may be used to eradicate the gram-negative bacteria in the periodontium.

The photosensitizer liquid or paste, when activated by an appropriate laser wavelength, produces hyperactive singlet oxygen that are capable of destroying bacteria. The oxygen singlets will destroy the gram-negative bacteria that are reacting with the inflammatory cells in the periodontium to mediate the inflammatory response. Specifically, the plasma cells elaborate antibodies against endotoxins, produced by the gram-negative bacteria, thereby producing antigen-antibody complexes that activate the complement system of the cat The result of complement activation is the production of biologically active substances such as anaphylatoxins, which mediate various aspects of the inflammatory response. By eradicating the gram-negative bacteria, the antigen-antibody complex that is responsible for initiating the inflammatory response is destroyed thereby effectively interrupting the chronic progression of the disease.

Particular pretreatment methods can be especially advantageous in treating periodontitis when used in conjunction with the present laser system. The laser treatment may be preceded by mechanically cleansing the surface of the teeth and by disinfecting the oral cavity with an antiplaque substance to remove the gram-negative bacteria on the surface of the teeth. Antimicrobial agents such as chloramphenicol, clindamycin, tetracycline or metronidazole may also be of some benefit prior to the dental procedure when the feline's immune system is suppressed due to a systemic illness. The photosensitizer may then be applied to the periodontium and a multi-wavelength laser system can be employed to activate the photosensitizer and to resect necrotic tissue at the roots of the periodontally involved teeth to eliminate the chronic symptoms associated with the condition. Additionally, the tubules may be sealed to further reduce the risk of infection.

Having described the preferred embodiments of the invention with reference to the accompanying drawings, it is to be understood that the invention is not limited to these precise embodiments, and that various changes and modifications may be effected therein by one skilled in the art without departing from the scope or spirit of the invention as defined in the appended claims.

What is claimed is:

1. A laser system for treating periodontal disease in felines comprising:
   a diode laser having an operating wavelength which is absorbed by feline oral tissue to achieve high precision, low penetrating cutting; wherein said operating wavelength can resect affected tissue and seal tubules;
   means to transport laser radiation of said wavelength from said laser to said feline oral tissue; and
   means of reducing risk of infection in said feline oral tissue.

2. A laser system according to claim 1 wherein said laser is operating at a wavelength absorbed by water moieties, at approximately 980 nm.

3. A laser system according to claim 1 wherein said laser has a multi-wavelength source that can resect affected tissue and seal tubules with one wavelength and can activate a photosensitizer with another wavelength.

4. A laser system according to claim 1 wherein said means to transport radiation is at least one optical fiber.

5. A laser system according to claim 1 wherein said laser radiation is delivered in a continuous mode to said oral tissue.

6. A laser system according to claim 1 wherein said laser radiation is delivered in a pulsed mode to said oral tissue.

7. A laser system according to claim 1 wherein said means of reducing risk of infection is a sealing of tubules to prevent microbial invasion, during and after treatment.

8. A treatment method for treating periodontal disease in felines comprising the steps of:
   positioning a laser having an operating wavelength which is absorbed by feline periodontal tissue, wherein said operating wavelength can resect affected tissue and seal tubules;

connecting to said laser, means to transport laser radiation to said feline periodontal tissue; and irradiating said periodontal (oral) tissue with radiation from said laser to resect affected tissue and to seal tubules to reduce risk of infection.

9. A treatment method according to claim 8 wherein said affected tissue is gingiva and it is resected to the cementoenamel junction.

10. A treatment method according to claim 8 wherein a second wavelength is added, one that will activate a photosensitizer, which can produce hyperactive singlet oxygen to further reduce risk of infection.

11. A treatment method according to claim 10 further comprising steps of:

applying a photosensitizer to said feline periodontal tissue prior to irradiation by said laser; and activating said photosensitizer with said laser's second wavelength.

12. A treatment method according to claim 8 further comprising pre-treatment steps of:

mechanically cleansing teeth to remove plaque containing gram negative bacteria; and disinfecting an oral cavity with an antiplaque substance.

13. A treatment method according to claim 12 further comprising a step of:

administering antibiotics to systemically ill felines prior to laser therapy.

14. A treatment method according to claim 11 wherein said affected tissue is gingiva and it is resected to the cementoenamel junction.

15. A treatment method according to claim 14 further comprising pre-treatment steps of:

mechanically cleansing teeth to remove plaque containing gram negative bacteria; and disinfecting an oral cavity with an antiplaque substance.

16. A treatment method according to claim 15 further comprising a step of:

administering antibiotics to systemically ill felines prior to laser therapy.

17. A treatment method according to claim 9 further comprising pre-treatment steps of:

mechanically cleansing teeth to remove plaque containing gram negative bacteria; and disinfecting an oral cavity with an antiplaque substance.

18. A treatment method according to claim 17 further comprising a step of:

administering antibiotics to systemically ill felines prior to laser therapy.

19. A treatment method according to claim 11 further comprising pre-treatment steps of:

mechanically cleansing teeth to remove plaque containing gram negative bacteria; and disinfecting an oral cavity with an antiplaque substance.

20. A treatment method according to claim 19 further comprising a step of:

administering antibiotics to systemically ill felines prior to laser therapy.

* * * * *

UNITED STATES PATENT AND TRADEMARK OFFICE
CERTIFICATE OF CORRECTION

PATENT NO.   : 5,941,701
DATED        : August 24, 1999
INVENTOR(S)  : K. Moran et al.

It is certified that error appears in the above-identified patent and that said Letters Patent is hereby corrected as shown below:

On the title page, insert item [73]  Assignee

-- CeramOptec Industries, Inc.
   515 Shaker Raod
   East Longmeadow, MA  01028

Signed and Sealed this

Twenty-first Day of November, 2000

Attest:

Q. TODD DICKINSON

*Attesting Officer*         *Director of Patents and Trademarks*